United States Patent [19]
McIver et al.

[11] Patent Number: 6,162,783
[45] Date of Patent: Dec. 19, 2000

[54] LIQUID DETERGENTS CONTAINING PROTEOLYTIC ENZYME AND PROTEASE INHIBITORS

[75] Inventors: John McMillan McIver, Cincinnati; Alan Carl Huber, Hamilton; Kirsten Louise McKillop, Cincinnati, all of Ohio

[73] Assignee: The Procter & Gamble Company, Cincinnati, Ohio

[21] Appl. No.: 09/147,981

[22] PCT Filed: Sep. 19, 1997

[86] PCT No.: PCT/US97/16623

§ 371 Date: May 27, 1999

§ 102(e) Date: May 27, 1999

[87] PCT Pub. No.: WO98/13460

PCT Pub. Date: Apr. 2, 1998

Related U.S. Application Data

[60] Provisional application No. 60/026,632, Sep. 24, 1996.

[51] Int. Cl.$^7$ ................................................. C11D 3/386
[52] U.S. Cl. ................ 510/320; 510/321; 510/226; 510/235; 510/300; 510/337; 510/339
[58] Field of Search .................. 510/226, 235, 510/300, 320, 321, 337, 339, 392, 393, 405, 465, 499

[56] References Cited

U.S. PATENT DOCUMENTS

| | | | |
|---|---|---|---|
| 4,261,868 | 4/1981 | Hora et al. | 252/529 |
| 4,318,818 | 3/1982 | Letton et al. | 252/174.12 |
| 4,399,065 | 8/1983 | Bajusz et al. | 260/112.5 |
| 4,404,115 | 9/1983 | Tai | 252/135 |
| 4,529,525 | 7/1985 | Dormal et al. | 252/132 |
| 4,537,706 | 8/1985 | Severson, Jr. | 252/545 |
| 4,537,707 | 8/1985 | Severson, Jr. | 252/545 |
| 4,566,985 | 1/1986 | Bruno et al. | 252/174.12 |
| 4,652,552 | 3/1987 | Kettner et al. | 514/18 |
| 4,703,036 | 10/1987 | Bajusz et al. | 514/18 |
| 5,030,378 | 7/1991 | Venegas | 252/174.12 |
| 5,234,829 | 8/1993 | Brown | 435/194 |
| 5,284,829 | 2/1994 | McKerrow et al. | 514/18 |
| 5,527,487 | 6/1996 | Mikkelsen et al. | 252/174.12 |
| 5,576,283 | 11/1996 | Johnston et al. | 510/321 |
| 5,582,762 | 12/1996 | Labeque et al. | 510/326 |
| 5,830,840 | 11/1998 | Johnston et al. | 510/392 |
| 5,840,678 | 11/1998 | Labeque et al. | 510/392 |

FOREIGN PATENT DOCUMENTS

| | | | |
|---|---|---|---|
| 0 130756 | 1/1985 | European Pat. Off. | C12N 15/00 |
| 0 185390 | 6/1986 | European Pat. Off. | C07K 5/08 |
| 0293881 | 12/1988 | European Pat. Off. | |
| 0 376 705 | 7/1990 | European Pat. Off. | C11D 3/86 |
| 0 381262 | 8/1990 | European Pat. Off. | C11D 3/386 |
| 0 473502 | 3/1992 | European Pat. Off. | A61K 7/48 |
| 0 511 456 | 11/1992 | European Pat. Off. | C11D 3/386 |
| 0 583534 | 2/1994 | European Pat. Off. | C11D 3/386 |
| 0 583536 | 2/1994 | European Pat. Off. | C11D 3/386 |
| 0583535 | 2/1994 | European Pat. Off. | |
| 90029670 | 9/1983 | Japan | C07C 125/06 |
| WO 92/03529 | 3/1992 | WIPO | C11D 3/386 |
| WO 92/05239 | 4/1992 | WIPO | C11D 3/386 |
| 93/00418 | 1/1993 | WIPO | |
| WO 93/13125 | 7/1993 | WIPO | C07K 3/00 |
| WO 94/04651 | 3/1994 | WIPO | C11D 3/386 |
| WO 94/04652 | 3/1994 | WIPO | C11D 3/386 |
| 95/24914 | 9/1995 | WIPO | |

OTHER PUBLICATIONS

Bajuszl et al., "Inhibition of Thrombin and Trypsin by Tripeptide Aldehydes", Int. J. Peptide Protein Res., vol. 12, pp. 217–221 (1978).

Nagy et al., "Tripeptide Aldehyde Protease Inhibitors May Depress in Vitro Prolactin and Growth Hormone Release", Endocrinology, vol. 116, No. 4, pp. 1426–1432 (1985).

*Primary Examiner*—Kery Fries
*Attorney, Agent, or Firm*—Kevin Waugh; C. Brant Cook; Kim Wm. Zerby

[57] ABSTRACT

Aqueous liquid detergent compositions are described which comprise a proteolytic enzyme wherein the proteolytic activity is reversibly inhibited by a peptide protease inhibitor selected from the group consisting of aldehydes and trifluoromethyl ketones.

21 Claims, No Drawings

LIQUID DETERGENTS CONTAINING PROTEOLYTIC ENZYME AND PROTEASE INHIBITORS

This application claims the benefit of provisional application 60/026,632, filed on Sep. 24, 1996.

TECHNICAL FIELD

This invention relates to liquid detergent compositions containing enzymes. More specifically, this invention pertains to liquid detergent compositions containing a detersive surfactant, a proteolytic enzyme, and a peptide protease inhibitor selected from the group consisting of peptide aldehydes and peptide trifluromethyl ketones.

BACKGROUND OF THE INVENTION

Protease-containing liquid aqueous detergents are well-known, especially in the context of laundry washing. A commonly encountered problem in such protease-containing liquid aqueous detergents is the degradation phenomenon by the proteolytic enzyme of second enzymes in the composition, such as amylase, lipase, and cellulase, or on the protease itself. As a result, the stability of the second enzyme or the protease itself in the detergent composition is affected and the detergent composition consequently performs less well.

In response to this problem, it has been proposed to use various protease inhibitors or stabilizers. For instance, various references have proposed the use of the following compounds to aid in the stabilization of enzymes: benzamidine hydrochloride, lower aliphatic alcohols or carboxylic acids, mixtures of a polyol and a boron compound, aromatic borate esters, and calcium, particularly calcium formate. Recently, it was discovered that certain peptide aldehydes and peptide trifluromethyl ketones act to stabilize protease enzyme.

Although these compounds have been used to varying success in liquid detergents, they are not free of problems. For example certain peptide aldehydes can be rather expensive and create complexities for the formulators, especially for liquid detergents. Other inhibitors such as calcium and boric acids are less expensive but do not stabilize enzymes as well as peptide aldehydes. It is thus an object of the present invention to provide alternate peptide aldehydes and trifluromethyl ketone protease inhibitors which are effective and suitable for use in a liquid detergent compositions.

BACKGROUND ART

It has been proposed to use various protease inhibitors or stabilizers. For instance, U.S. Pat. No. 4,566,985 proposes to use benzamidine hydrochloride; EP 376 705 proposes to use lower aliphatic alcohols or carboxylic acids; EP 381 262 proposes to use a mixture of a polyol and a boron compound; and EP 91870072.5 proposes to use aromatic borate esters. See also U.S. Pat. No. 5,030,378 issued Jul. 9, 1991. Also see U.S. Pat. No. 4,261,868; U.S. Pat. No. 4,404,115; U.S. Pat. No. 4,318,818; and EP 130,756.

The use of peptide derivatives for the inhibition of proteins appears to have been disclosed in therapeutic applications. EP 293 881 discloses the use of peptide boronic acids as inhibitors of trypsin-like serine proteases. EP 185 390 and U.S. Pat. No. 4,399,065 disclose the use of certain peptide aldehydes derivatives for the inhibition of blood coagulation. J 90029670 discloses the use of optically active alpha amino aldehydes for the inhibition of enzymes in general. See also "Inhibition of Thrombin and Trypsin by Tripeptide Aldehydes", *Int. J. Peptide Protein Res.*, Vol 12 (1978), pp. 217–221; Gaal, Bacsy & Rappay, and "Tripeptide Aldehyde Protease Inhibitors May Depress in Vitro Prolactin and Growth Hormone Release" *Endocrinology*, Vol. 116, No. 4 (1985), pp. 1426–1432; Rappay, Makara, Bajusz & Nagy. Certain peptide aldehydes have also been disclosed in EP-A-473 502 for inhibiting protease-mediated skin irritation.

In particular see EP185,390, WO 94/04651, published Mar. 3, 1994, WO 94104652, published Mar. 3, 1994, EP 583,536, published Feb. 23, 1994, EP 583,535, published Feb. 3, 1994, EP 583,534, published Feb. 23, 1994, WO 93/13125, published Jul. 8, 1993, U.S. Pat. No. 4,529,525, U.S. Pat. No. 4,537,706, U.S. Pat. No. 4,537,707, and U.S. Pat. No. 5,527,487.

SUMMARY OF THE INVENTION

The invention herein is a liquid detergent composition comprising:

a) an effective amount of a detersive surfactant;
b) an active proteolytic enzyme; and
c) a peptide protease inhibitor having the formula:

$$Z-B-NH-CH(R)-C(O)-X$$

wherein B is a peptide chain comprising from 2 to 5 amino acid moieties; X is hydrogen or $CF_3$; Z is an N-capping moiety selected from the group consisting of sulfonamides, phosphoramidates, thioureas, sulfenamides, sulfonic acids, phosphinamides, thiocarbamates, amidophosphates, sulfamoyl derivatives, and phosphonamides; and R is selected from the group consisting of straight or branched $C_1-C_6$ unsubstituted alkyl, phenyl, and $C_7-C_9$ alkylaryl moieties. Preferred compositions further comprise a source of calcium ion or boric acid.

Preferably, the liquid detergent compositions herein comprise, by weight of composition:

a) from about 1 to about 95%, preferably from about 8% to about 70%, of said detersive surfactant;
b) from about 0.0001% to about 5%, preferably from about 0.0003% to about 0.1%, of an active proteolytic enzyme;
c) from about 0.00001% to about 5%, preferably from about 0.0001% to about 1%, more preferably from about 0.0006% to about 0.5%, of the described peptide protease inhibitor;
d) optionally, from about 0.01% to about 1%, preferably from about 0.05% to about 0.5%, of calcium ion; and
e) optionally, from about 0.25% to about 10%, preferably from about 0.5% to about 5%, of boric acid or a compound capable of forming boric acid, preferably with a diol.

The proteolytic enzyme useful herein is preferably a subtilisin-type protease and may be selected from the group consisting of Alcalase®, Subtilisin BPN', Protease A, Protease B, and mixtures thereof.

The source of calcium ion for use herein is preferably selected from calcium formate, calcium xylene sulfonate, calcium chloride, calcium acetate, calcium sulfate, and mixtures thereof.

The dishcare compositions herein may contain further detersive adjuncts, including but not limited to, one or more of the following: suds boosters, chelants, polyacrylate polymers, dispersing agents, dyes, perfumes, processing aids, and mixtures thereof. Moreover for dishcare compositions, the liquid detergent compositions may further comprise an effective amount of amylase enzyme. Additionally, the dishcare compositions may optionally comprise an effective amount of a source of boric acid and a diol. Typically dishcare compositions will optionally, but preferably, comprise from about 0.25% to about 10%, preferably from about 0.5% to about 5%, more preferably from about 0.75% to about 3%, by weight of boric acid or a compound capable of forming boric acid and a diol, e.g. 1,2-propaneidiol.

In a preferred embodiment for heavy duty detergent compositions useful in laundry care, the liquid detergent composition further comprises an effective amount one or more of the following enzymes: lipase, amylase, cellulase, and mixtures thereof. Preferably for laundry compositions, the second enzyme is lipase and is obtained by cloning the gene from *Humicola Lanuginosa* and expressing the gene in *Aspergillus Oryzae*. Lipase is utilized in an amount of from about 10 to about 18000 lipase units per gram, preferably from about from about 60 to about 6000 units per gram.

In another preferred composition useful for laundry care, the second enzyme is a cellulase derived from *Humicola Insolens* and is utilized in an amount of from about 0.0001% to about 0.1% by weight of the total composition of said cellulase.

The compositions herein may contain further detersive adjuncts, including but not limited to, one or more of the following: suds boosters, builders, soil release polymers, polyacrylate polymers, dispersing agents, dye transfer inhibitors, dyes, perfumes, processing aids, brighteners, and mixtures thereof. Additionally, for laundrycare compositions, the detersive surfactant is typically present in an amount of from about 10% to about 70%, by weight of total composition. Moreover, the laundry compositions may optionally comprise an effective amount of a source of boric acid and a diol. Typically laundry compositions will optionally, but preferably, comprise from about 0.25% to about 10%, preferably from about 0.5% to about 5%, more preferably from about 0.75% to about 3%, by weight of boric acid or a compound capable of forming boric acid and a diol, e.g. 1,2-propaneidiol.

All percentages and proportions herein are by weight, and all references cited are hereby incorporated by reference, unless otherwise specifically indicated.

DETAILED DESCRIPTION OF THE INVENTION

Definitions—The present detergent compositions comprise an "effective amount" or a "stain removal-improving amount" of individual components defined herein. An "effective amount" or "stain removal-improving amount" is any amount capable of measurably improving soil cleaning or stain removal from a substrate, i.e., soiled fabric or soiled dishware, when it is washed by the consumer. In general, this amount may vary quite widely.

The liquid aqueous detergent compositions according to the present invention comprise three essential ingredients: (A) a peptide protease inhibitor selected from the group consisting of aldehydes and trifluoromethyl ketones, or a mixture thereof, as described herein, (B) a proteolytic enzyme or a mixture thereof, and (C) a detersive surfactant. The compositions according to the present invention preferably further comprise (D) a source of calcium ions, (E) a detergent-compatible second enzyme or a mixture thereof, (F) boric acid and a diol, and may further comprise (G) other optional ingredients.

Peptide protease inhibitors—The detergent compositions according to the present invention comprise, as a first essential ingredient, a peptide protease inhibitor selected from the group consisting of aldehydes and trifluoromethyl ketones, or mixtures thereof, having the formula:

Z—B—NH—CH(R)—C(O)—X wherein B is a peptide chain comprising from 2 to 5 amino acid moieties; X is hydrogen or $CF_3$; Z is an N-capping moiety selected from the group consisting of phosphoramidate [(R"O)$_2$(O)P—], sulfenamide [(SR")$_2$—], sulfonamide [(R"(O)$_2$S—], sulfonic acid [SO$_3$H], phosphinamide [(R")$_2$(O)P—], sulfamoyl derivative [R"O(O)2S—], thiourea [(R")$_2$N(O)C—], thiocarbamate [R"O(S)C—], phosphonate [R"P(O)OH], and amidophosphate [R"O(OH)(O)P—], wherein each R" is independently selected from the group consisting of straight or branched $C_1$–$C_6$ unsubstituted alkyl, phenyl, $C_7$–$C_9$ alkylaryl, and cycloalkyl moieties, wherein the cycloalkyl ring may span $C_4$–$C_8$ and may contain one or more heteroatoms selected from the group consisting of O, N, and S; and R is selected from the group consisting of straight or branched $C_1$–$C_6$ unsubstituted alkyl, phenyl, and $C_7$–$C_9$ alkylaryl moieties.

Preferred R moieties are selected from the group consisting of methyl, iso-propyl, sec-butyl, iso-butyl, —$C_6H_5$, —$CH_2$—$C_6H_5$, and —$CH_2CH_2$—$C_6H_5$, which respectively may be derived from the amino acids Ala, Val, Ile, Leu, PGly (phenylglycine), Phe, and HPhe (homophenylalanine) by converting the carboxylic acid group to an aldehyde or trifluromethyl ketone group. While such moieties are therefore not amino acids (and they may or may not have been synthesized from an amino acid precursor), for purposes of simplification of the exemplification of inhibitors useful here, the aldehyde portion of the inhibitors are indicated as derived from amino acids by the addition of "H" after the analogous amino acid [e.g., "—AlaH" represents the chemical moiety "—NHCH($CH_3$)C(O)H"]. Trifluoromethyl ketones are similarly represented by the addition of "$CF_3$" after the analogous amino acid (e.g., "—Ala$CF_3$" represents the chemical moiety "—NHCH($CH_3$)C(O)$CF_3$"].

Preferred B peptide chains are selected from the group consisting of peptide chains having the amino acid sequences according to the general formula:

Z—$A^5$—$A^4$—$A^3$—$A^2$—$A^1$—NH—CH(R)—C(O)—X such that the following amino acids, when present, are:

$A^1$ is selected from Ala, Gly;

$A^2$ is selected from Val, Ala, Gly, Ile;

$A^3$, if present, is selected from Phe, Leu, Val, Ile;

$A^4$, if present, is any amino acid, but preferably is selected from Gly, Ala;

$A^5$, if present, is any amino acid, but preferably is Gly, Ala, Lys.

The present invention aldehydes may be prepared from the corresponding amino acid whereby the C-terminal end of said amino acid is converted from a carboxylic group to an aldehyde group. Such aldehydes may be prepared by known processes, for instance as described in U.S. Pat. No. 5015627, EP 185 930, EP 583,534, and DE 32 00 812.

The present invention trifluoromethyl ketones may be prepared from the corresponding amino acid whereby the C-terminal end of said amino acid is converted from a carboxylic group to the trifluoromethyl ketone group. Such trifluoromethyl ketones may be prepared by known processes, for instance as described in EP 583,535.

While not wanting to be bound by theory it is believed that the peptide protease inhibitors according to the present invention bind to the proteolytic enzyme in the liquid detergent composition, thereby inhibiting said proteolytic enzyme. Upon dilution in water, the proteolytic activity is restored by dissociation of the proteolytic enzyme/peptide protease inhibitor complex.

The N-terminal end of said protease inhibitors according to the present invention is protected by one of the N-capping moiety protecting groups selected from the group consisting of sulfonamides, phosphonamides, thioureas, sulfenamides, sulfonic acids, phosphinamides, thiocarbamates, amidophosphates, and phosphonamides. However, in a highly preferred embodiment of the present invention, the N-terminal end of said protease inhibitor is protected by a methyl, ethyl or benzyl sulfonamide [$CH_3SO_2$—; $CH_3CH_2SO_2$—; or $C_6H_5CH_2SO_2$—], and methyl, ethyl or benzyl amidophosphate [$CH_3O(OH)(O)P$—; $CH_3CH_2O(OH)(O)P$—; or $C_6H_5CH_2O(OH)(O)P$—] groups.

Synthesis of N-capping groups can be found in the following references: *Protective Groups in Organic Chemistry*, Greene, T., Wuts, P., John Wiley & Sons, New York, 1991, pp 309–405; March, J, *Advanced Organic Chemistry*, Wiley Interscience, 1985, pp. 445, 469, Carey, F. Sundberg, R., *Advanced Organic Chemistry*, Part B, Plenum Press, New York, 1990, pp. 686–89; Atherton, E., Sheppard, R., *Solid Phase Peptide Synthesis*, Pierce Chemical, 1989, pp. 3–4; Grant, G., *Synthetic Peptides*, W. H. Freeman & Co. 1992, pp. 77–103; Stewart, J., Young, J., *Solid Phase Peptide Synthesis*, 2nd Edition, IRL Press, 1984, pp. 3,5,11, 14–18, 28–29. Bodansky, M., *Principles of Peptide Synthesis*, Springer-Verlag, 1988, pp. 62, 203, 59–69; Bodansky, M., *Peptide Chemistry*, Springer-Verlag, 1988, pp. 74–81, Bodansky, M., Bodansky, A., *The Practice of Peptide Synthesis*, Springer-Verlag, 1984, pp. 9–32.

Examples of protease inhibitors for use herein are: $CH_3SO_2$Phe-Gly-Ala-Leu-H, $CH_3SO_2$Val-Ala-Leu-H, $C_6H_5CH_2O(OH)(O)P$-Val-Ala-Leu-H, $C_6H_5CH_2O(OH)(O)P$-Val-Ala-Leu-$CF_3$, $CH_3CH_2SO_2$-Phe-Gly-Ala-Leu-H, $C_6H_5CH_2SO_2$-Val-Ala-Leu-H, $C_6H_5CH_2O(OH)(O)P$-Leu-Ala-Leu-H, $C_6H_5CH_2O(OH)(O)P$-Phe-Ala-Leu-H, $CH_2O(OH)(O)P$-Leu-Gly-Ala-Leu-H.

In the Synthesis Examples hereinafter methods are disclosed to synthesize certain of these peptide protease inhibitors.

SYNTHESIS EXAMPLE 1

Synthesis of the tripeptide trifluoromethylketone Moc-Phe-Gly-Ala-Leu$CF_3$ (a) N-trityl-leucine methyl ester: To a solution of 2.50 g (13.8 mmol) of Leu-OMe.HCl in 100 ml $CH_2Cl_2$ is added 3.86 ml TEA (27.5 mmol) dropwise. After the addition is complete 3.76 g (13.5 mmol) of triphenylmethyl chloride in 15 ml $CH_2Cl_2$ is added dropwise. The mixture is stirred for 4 H. The solution is diluted with 5% EtOAc/petroleum ether and washed with water. The organic phase is dried ($MgSO_4$) filtered and the solvent removed. The residue is chromatographed on silica to give 4.8 g of pure product (90% yield).

(b) N-trityl-leucinal: To a cold (0°) solution of 4.70 g (12.2 mmol) of N-trityl-leucine methyl ester in 100 ml THF is added 28.1 ml of a 1.5M solution of diisobutylaluminum hydride (42.2 mol) in THF dropwise. The solution is stirred for 6 h at this temperature and the reaction quenched with saturated Na—K tartrate, extracted with EtOAc, dried ($MgSO_4$), filtered and the solvent is removed. Recovered 4.13 g of the desired material that is used without purification. To a solution of 1.29 g (14.9 mmol) of oxalyl chloride in 20 ml $CH_2Cl_2$ at −78° C. is added 2.26 ml DMSO (29.8 mmol) in 5 ml $CH_2Cl_2$ dropwise. After the addition is complete, 4.13 g (11.5 mmol) of crude N-trityl-leucinol in 10 ml $CH_2Cl_2$ is added. The solution is warmed to 0° C. and poured into a mixture of water and ether. The phases are separated and the ether phase dried ($MgSO_4$) and evaporated to afford 1.37 g of the desired compound.

(c) 5-Methyl-3-tritylamino-1,1,1-trifluoro-2-hexanol: To a solution of 1.37 g (3.83 mmol) of N-trityl-leucinal and 0.653 ml (4.59 mmol) of $CF_3$TMS in THF is added 0.121 g (0.383 mmol) of tetrabutylammonium fluoride trihydrate in one portion. The solution is stirred for 3 h at room temperature and the solvent removed. The residue is dissolved in EtOAc, washed with water, dried ($MgSO_4$), and the solvent removed to afford 1.20 g of the product that is chromatographed on silica (0.760 g pure product).

d) 3-(N-(Cbz-Gly-Ala))-5-methyl-1,1,1-trifluoro-2-hexanol: To a solution of 1.21 g (2.83 mmol) of 5-methyl-3-tritylamino-1,1,1-trifluoro-2-hexanol in 10 ml dioxane is added 5 ml of 4.0 M HCl in dioxane. The solution is stirred for 2 h at room temperature and the solvent removed. The residue is triturated with ether and the solid material filtered. The resulting HCl salt (0.627 g, 2.83 mmol) is suspended in 10 ml $CH_2Cl_2$ and Z-Gly-Ala-OH added (0.793 g, 2.83 mmol). To this mixture is added 0.870 ml (6.23 mmol) TEA followed immediately by the addition of 0.473 ml (3.12 mmol) of DEPC. The mixture is stirred overnight and the solvent removed. The residue is dissolved in EtOAc and washed with 1N HCl, saturated $NaHCO_3$, and brine. The solution of product is dried ($MgSO_4$), filtered and the solvent removed to give 1.06 g product.

(e) 3-N-(Ms-Phe-Gly-Ala))-5-methyl-1,1,1-trifluoro-2-hexanol: To a solution of 1.06 g (2.37 mmol) of 3-(N-Cbz-Gly-Ala)-5-methyl-1,1,1-trifluoro-2-hexanol in 5 ml of MeOH is added 0.35 g Pd/C. The slurry is degassed and hydrogenated under a positive pressure of hydrogen overnight. The slurry is filtered through Celite and the solvent removed. The residue is dissolved in $CH_2Cl_2$ and 0.898 g (22.37 mmol) of Ms-Phe-OH added. To this mixture is added 0.732 ml (5.22 mmol) of TEA, followed by the addition of 0.395 ml (2.61 mmol) of DEPC. The solution is stirred overnight and the solvent removed. The residue is chromatographed on silica to afford 0.720 g pure product.

(f) Ms-Phe-Gly-Ala-Leu$CF_3$: To a slurry of 1.59 g (3.75 mmol) of Dess-Martin periodinane in 15 ml $CH_2Cl_2$ is added 0.650 g (1.25 mmol) of 3-(N-Ms-Phe-Gly-Ala)-5-methyl-1,1,1-trifluoro-2-hexanol in 5 ml $CH_2Cl_2$ and the slurry stirred for 3 h. To this mixture is added 6.51 g (25.2 mmol) of $Na2SO_2O_3$ in saturated $NaHCO_3$ and the resulting solution stirred for 10 min. The solution is extracted with EtOAc and the organic phase dried ($MgSO_4$), filtered and the solvent removed. The residue is chromatographed on silica to afford 0.445 g of pure product.

SYNTHESIS EXAMPLE 2

Synthesis of Ms-Phe-Gly-Ala-LeuH (a) Ms-Phe-Gly-OH: To a solution of 2.0 g (9.0 mmol) Phe-Gly-OH, which is dissolved in 9 ml 1N NaOH and cooled to 0° C., is added simultaneously 0.766 ml (9.9 mmol) of methane sulfonyl chloride and 9 ml 1N NaOH, in separate addition funnels. After addition is complete the reaction is stirred 15 minutes at 0° C. and 1 h at room temperature. At this point the solution is cooled to 0° C., the pH adjusted to 9.5 and is washed with EtOAc (1×, 50 ml). The aqueous phase (0° C.) is then adjusted to pH=2.5 (2N HCl) and extracted with EtOAc (3×, 50 ml), dried ($MgSO_4$), filtered, and the solvent removed to afford 2.0 g pure product.

(b) Ms-Phe-Gly-Ala-Leucinol: A solution of is prepared by dissolving 0.500 g (1.67 mmol) N-Ms-Phe-Gly-OH in 15 ml THF, cooling to −15° C., and adding 0.366 ml (3.33 mmol) NMM followed by 0.216 ml (1.67 mmol) isobutyl chloroformate. This solution is stirred 5 minutes and 0.374 g (1.67 mmol) Ala-Leucinol.HCl, in a mixture of 10 ml THF and minimal DMF, are added. Stirring is continued at 0° C. for 15 minutes and 2 h at room temperature. The solution is quenched with 5 ml 1N HCl, extracted with EtOAc (3×, 50 ml), the combined extracts are washed with sat'd NaHCO$_3$ and sat'd NaCl. The resulting organic phase is then dried (MgSO$_4$), filtered, evaporated and chromatographed on silica to yield 0.260 g of the desired material.

(c) Ms-Phe-Gly-Ala-LeuH: A solution is prepared by adding 0.337 g (0.798 mmol) Dess-Martin periodinane to 5 ml CH$_2$Cl$_2$ and stirring for 10 minutes. To this solution 0.125 g (0.266 mmol) N-Ms-Phe-Gly-Ala-Leucinol is added in one portion. The reaction is continued until TLC showed complete conversion at which time the solution is poured into 25 ml sat'd NaHCO$_3$ containing 1.8 g (5.586 mmol) Na$_2$S$_2$O$_3$. After stirring for 10 minutes the mixture is extracted with EtOAc (3×, 50 ml). The combined extracts are dried (MgSO$_4$), evaporated, and chromatographed on silica to afford 0.048 g of the product.

Gly=glycine

Ala=alanine

Leu=leucine

Phe=phenylalanine

OMe=methyl ester

TEA=triethylamine

DECP=diethylcyanophosphonate

TLC=thin layer chromatography

MeOH=methanol

Pd/C=palladium on activated carbon

EtOH=ethanol

THF=tetrahydrofuran

Ms=methanesulfonyl

Proteolytic Enzyme—Another essential ingredient in the present liquid detergent compositions is active proteolytic enzyme. Mixtures of proteolytic enzyme are also included. The proteolytic enzyme can be of animal, vegetable or microorganism (preferred) origin. The proteases for use in the detergent compositions herein include (but are not limited to) trypsin, subtilisin, chymotrypsin and elastase-type proteases. Preferred for use herein are subtilisin-type proteolytic enzymes. Particularly preferred is bacterial serine proteolytic enzyme obtained from *Bacillus subtilis* and/or *Bacillus licheniformis*. Protease enzymes are usually present in such liquid detergent compositions at levels sufficient to provide from 0.005 to 0.1 Anson units (AU) of activity per gram of composition.

Suitable proteolytic enzymes include Novo Industri A/S Alcalase® (preferred), Esperase®, Savinase® (Copenhagen, Denmark), Gist-brocades' Maxatase®, Maxacal® and Maxapem 15® (protein engineered Maxacal®) (Delft, Netherlands), and subtilisin BPN and BPN' (preferred), which are commercially available. Preferred proteolytic enzymes are also modified bacterial serine proteases, such as those made by Genencor International, Inc. (San Francisco, Calif.) which are described in European Patent 251,446, filed Apr. 28, 1987 (particularly pages 17, 24 and 98), and which is called herein "Protease B", and U.S. Pat. No. 5,030,378, Venegas, issued Jul. 9, 1991, which refers to a modified bacterial serine proteolytic enzyme (Genencor International) which is called "Protease A" herein (same as BPN'). In particular see columns 2 and 3 of U.S. Pat. No. 5,030,378 for a complete description, including amino sequence, of Protease A and its variants. Preferred proteolytic enzymes, then, are selected from the group consisting of Alcalase® (Novo Industri A/S), BPN', Protease A and Protease B (Genencor), and mixtures thereof. Protease B is most preferred.

Another preferred protease, referred to as "Protease D" is a carbonyl hydrolase variant having an amino acid sequence not found in nature, which is derived from a precursor carbonyl hydrolase by substituting a different amino acid for a plurality of amino acid residues at a position in said carbonyl hydrolase equivalent to position +76, preferably also in combination with one or more amino acid residue positions equivalent to those selected from the group consisting of +99, +101, +103, +104, +107, +123, +27, +105, +109, +126, +128, +135, +156, +166, +195, +197, +204, +206, +210, +216, +217, +218, +222, +260, +265, and/or +274 according to the numbering of *Bacillus amyloliquefaciens* subtilisin, as described in WO 95/10615 published Apr. 20, 1995 by Genencor International.

Useful proteases are also described in PCT publications: WO 95/30010 published Nov. 9, 1995 by The Procter & Gamble Company; WO 95/30011 published Nov. 9, 1995 by The Procter & Gamble Company; WO 95/29979 published Nov. 9, 1995 by The Procter & Gamble Company.

Detersive Surfactant—An effective amount, typically from about 1 to 95, preferably about 8 to 70, weight %, of detersive surfactant is yet another essential ingredient in the present invention. The detersive surfactant can be selected from the group consisting of anionics, nonionics, cationics, ampholytics, zwitterionics, and mixtures thereof. By selecting the type and amount of detersive surfactant, along with other adjunct ingredients disclosed herein, the present detergent compositions can be formulated to be used in the context of laundry cleaning or in other different cleaning applications, particularly including dishwashing. The particular surfactants used can therefore vary widely depending upon the particular end-use envisioned.

The benefits of the present invention are especially pronounced in compositions containing ingredients that are harsh to enzymes such as certain detergency builders and surfactants. These include (but are not limited to) anionic surfactants such as alkyl ether sulfate linear alkyl benzene sulfonate, alkyl sulfate, etc. Suitable surfactants are described below.

Anionic Surfactants—One type of anionic surfactant which can be utilized encompasses alkyl ester sulfonates. These are desirable because they can be made with renewable, non-petroleum resources. Preparation of the alkyl ester sulfonate surfactant component can be effected according to known methods disclosed in the technical literature. For instance, linear esters of $C_8$–$C_{20}$ carboxylic acids can be sulfonated with gaseous SO$_3$ according to "The Journal of the American Oil Chemists Society," 52 (1975), pp. 323–329. Suitable starting materials would include natural fatty substances as derived from tallow, palm, and coconut oils, etc.

The preferred alkyl ester sulfonate surfactant, especially for laundry applications, comprises alkyl ester sulfonate surfactants of the structural formula:

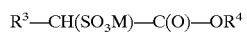

wherein $R^3$ is a $C_8$–$C_{20}$ hydrocarbyl, preferably an alkyl, or combination thereof, $R^4$ is a $C_1$–$C_6$ hydrocarbyl, preferably an alkyl, or combination thereof, and M is a soluble salt-forming cation. Suitable salts include metal salts such as sodium, potassium, and lithium salts, and substituted or unsubstituted ammonium salts, such as methyl-, dimethyl, -trimethyl, and quaternary ammonium cations, e.g. tetramethyl-ammonium and dimethyl piperdinium, and cations derived from alkanolamines, e.g. monoethanol-amine, diethanolamine, and triethanolamine. Preferably, $R^3$ is $C_{10}$–$C_{16}$ alkyl, and $R^4$ is methyl, ethyl or isopropyl. Especially preferred are the methyl ester sulfonates wherein $R^3$ is $C_{14}$–$C_{16}$ alkyl.

Alkyl sulfate surfactants are another type of anionic surfactant of importance for use herein. In addition to providing excellent overall cleaning ability when used in combination with polyhydroxy fatty acid amides (see below), including good grease/oil cleaning over a wide range of temperatures, wash concentrations, and wash times, dissolution of alkyl sulfates can be obtained, as well as improved formulability in liquid detergent formulations are water soluble salts or acids of the formula $ROSO_3M$ wherein R preferably is a $C_{10}$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali metal cation (e.g., sodium, potassium, lithium), substituted or unsubstituted ammonium cations such as methyl-, dimethyl-, and trimethyl ammonium and quaternary ammonium cations, e.g., tetramethyl-ammonium and dimethyl piperdinium, and cations derived from alkanolamines such as ethanolamine, diethanolamine, triethanolamine, and mixtures thereof, and the like. Typically, alkyl chains of $C_{12}$–$C_{16}$ are preferred for lower wash temperatures (e.g., below about 50° C.) and $C_{16}$–$C_{18}$ alkyl chains are preferred for higher wash temperatures (e.g., above about 50° C.).

Alkyl alkoxylated sulfate surfactants are another category of useful anionic surfactant. These surfactants are water soluble salts or acids typically of the formula $RO(A)_mSO_3M$ wherein R is an unsubstituted $C_{10}$–$C_{24}$ alkyl or hydroxyalkyl group having a $C_{10}$–$C_{24}$ alkyl component, preferably a $C_{12}$–$C_{20}$ alkyl or hydroxyalkyl, more preferably $C_{12}$–$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl-, trimethyl-ammonium and quaternary ammonium cations, such as tetramethyl-ammonium, dimethyl piperidinium and cations derived from alkanolamines, e.g. monoethanolamine, diethanolamine, and triethanolamine, and mixtures thereof. Exemplary surfactants are $C_{12}$–$C_{18}$ alkyl polyethoxylate (1.0) sulfate, $C_{12}$–$C_{18}$ alkyl polyethoxylate (2.25) sulfate, $C_{12}$–$C_{18}$ alkyl polyethoxylate (3.0) sulfate, and $C_{12}$–$C_{18}$ alkyl polyethoxylate (4.0) sulfate wherein M is conveniently selected from sodium and potassium.

Other Anionic Surfactants—Other anionic surfactants useful for detersive purposes can also be included in the compositions hereof. These can include salts (including, for example, sodium, potassium, ammonium, and substituted ammonium salts such as mono-, di- and triethanolamine salts) of soap, $C_9$–$C_{20}$ linear alkylbenzenesulphonates, $C_8$–$C_{22}$ primary or secondary alkanesulphonates, $C_8$–$C_{24}$ olefinsulphonates, sulphonated polycarboxylic acids prepared by sulphonation of the pyrolyzed product of alkaline earth metal citrates, e.g., as described in British patent specification No. 1,082,179, alkyl glycerol sulfonates, fatty acyl glycerol sulfonates, fatty oleyl glycerol sulfates, alkyl phenol ethylene oxide ether sulfates, paraffin sulfonates, alkyl phosphates, isothionates such as the acyl isothionates, N-acyl taurates, fatty acid amides of methyl tauride, alkyl succinamates and sulfosuccinates, monoesters of sulfosuccinate (especially saturated and unsaturated $C_{12}$–$C_{18}$ monoesters) diesters of sulfosuccinate (especially saturated and unsaturated $C_6$–$C_{14}$ diesters), N-acyl sarcosinates, sulfates of alkylpolysaccharides such as the sulfates of alkylpolyglucoside (the nonionic nonsulfated compounds being described below), branched primary alkyl sulfates, alkyl polyethoxy carboxylates such as those of the formula $RO(CH_2CH_2O)_kCH_2COO$—$M^+$ wherein R is a $C_8$–$C_{22}$ alkyl, k is an integer from 0 to 10, and M is a soluble salt-forming cation, and fatty acids esterified with isethionic acid and neutralized with sodium hydroxide. Resin acids and hydrogenated resin acids are also suitable, such as rosin, hydrogenated rosin, and resin acids and hydrogenated resin acids present in or derived from tall oil. Further examples are given in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23 (herein incorporated by reference).

Nonionic Detergent Surfactants—Suitable nonionic detergent surfactants are generally disclosed in U.S. Pat. No. 3,929,678, Laughlin et al., issued Dec. 30, 1975, at column 13, line 14 through column 16, line 6, incorporated herein by reference. Exemplary, non-limiting classes of useful nonionic surfactants are listed below.

The polyethylene, polypropylene, and polybutylene oxide condensates of alkyl phenols. In general, the polyethylene oxide condensates are preferred. These compounds include the condensation products of alkyl phenols having an alkyl group containing from about 6 to about 12 carbon atoms in either a straight chain or branched chain configuration with the alkylene oxide. In a preferred embodiment, the ethylene oxide is present in an amount equal to from about 5 to about 25 moles of ethylene oxide per mole of alkyl phenol. Commercially available nonionic surfactants of this type include Igepal® CO-630, marketed by the GAF Corporation; and Triton® X-45, X-114, X-100, and X-102, all marketed by the Rohm & Haas Company. These compounds are commonly referred to as alkyl phenol alkoxylates, (e.g., alkyl phenol ethoxylates).

The condensation products of aliphatic alcohols with from about 1 to about 25 moles of ethylene oxide. The alkyl chain of the aliphatic alcohol can either be straight or branched, primary or secondary, and generally contains from about 8 to about 22 carbon atoms. Particularly preferred are the condensation products of alcohols having an alkyl group containing from about 10 to about 20 carbon atoms with from about 2 to about 18 moles of ethylene oxide per mole of alcohol. Examples of commercially available nonionic surfactants of this type include Tergitol® 15-S-9 (the condensation product of $C_{11}$–$C_{15}$ linear secondary alcohol with 9 moles ethylene oxide), Tergitol® 24-L-6 NMW (the condensation product of $C_{12}$–$C_{14}$ primary alcohol with 6 moles ethylene oxide with a narrow molecular weight distribution), both marketed by Union Carbide Corporation; Neodol® 45-9 (the condensation product of $C_{14}$–$C_{15}$ linear alcohol with 9 moles of ethylene oxide), Neodol® 23-6.5 (the condensation product of $C_{12}$–$C_{13}$ linear alcohol with 6.5 moles of ethylene oxide), Neodol® 45-7 (the condensation product of $C_{14}$–$C_{15}$ linear alcohol with 7 moles of ethylene oxide), Neodol® 45-4 (the condensation product of $C_{14}$–$C_{15}$ linear alcohol with 4 moles of ethylene oxide), marketed by Shell Chemical Company, and Kyro® EOB (the condensation product of $C_{13}$–$C_{15}$ alcohol with 9 moles ethylene oxide), marketed by The Procter & Gamble Company. This category of nonionic surfactant is referred to generally as "alkyl ethoxylates."

The condensation products of ethylene oxide with a hydrophobic base formed by the condensation of propylene oxide with propylene glycol. The hydrophobic portion of these compounds preferably has a molecular weight of from about 1500 to about 1800 and exhibits water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially-available Pluronic® surfactants, marketed by BASF.

The condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000.

Examples of this type of nonionic surfactant include certain of the commercially available Tetronic® compounds, marketed by BASF.

Semi-polar nonionic surfactants are a special category of nonionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety of from about 10 to about 18 carbon atoms and a moiety selected from the group consisting of alkyl and hydroxyalkyl moieties of from about 1 to about 3 carbon atoms.

Semi-polar nonionic detergent surfactants include the amine oxide surfactants having the formula $$R^3(OR^4)_xN(O)(R^5)_2$$

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof, x is from 0 to about 3; and each $R^5$ is an alkyl or hydroxyalkyl group containing from about 1 to about 3 carbon atoms or a polyethylene oxide group containing from about 1 to about 3 ethylene oxide groups. The $R^5$ groups can be attached to each other, e.g., through an oxygen or nitrogen atom, to form a ring structure.

These amine oxide surfactants in particular include $C_{10}$–$C_{18}$ alkyl dimethyl amine oxides and $C_8$–$C_{12}$ alkoxy ethyl dihydroxy ethyl amine oxides.

Alkylpolysaccharides disclosed in U.S. Pat. No. 4,565, 647, Llenado, issued Jan. 21, 1986, having a hydrophobic group containing from about 6 to about 30 carbon atoms, preferably from about 10 to about 16 carbon atoms and a polysaccharide, e.g., a polyglycoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6- positions on the preceding saccharide units.

Optionally, and less desirably, there can be a polyalkylene-oxide chain joining the hydrophobic moiety and the polysaccharide moiety. The preferred alkyleneoxide is ethylene oxide. Typical hydrophobic groups include alkyl groups, either saturated or unsaturated, branched or unbranched containing from about 8 to about 18, preferably from about 10 to about 16, carbon atoms. Preferably, the alkyl group is a straight chain saturated alkyl group. The alkyl group can contain up to about 3 hydroxy groups and/or the polyalkyleneoxide chain can contain up to about 10, preferably less than 5, alkyleneoxide moieties. Suitable alkyl polysaccharides are octyl, nonyl, decyl, undecyldodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses and/ or galactoses. Suitable mixtures include coconut alkyl, di-, tri-, tetra-, and pentaglucosides and tallow alkyl tetra-, penta-, and hexa-glucosides.

The preferred alkylpolyglycosides have the formula $$R^2O(C_nH_{2n}O)_t(glycosyl)_x$$

wherein $R^2$ is selected from the group consisting of alkyl, alkyl-phenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

Fatty acid amide surfactants having the formula:

$$R^6\text{---}C(O)\text{---}N(R^7)_2$$

wherein $R^6$ is an alkyl group containing from about 7 to about 21 (preferably from about 9 to about 17) carbon atoms and each $R^7$ is selected from the group consisting of hydrogen, $C_1$–$C_4$ alkyl, $C_1$–$C_4$ hydroxyalkyl, and —$(C^2H_4O)_xH$ where x varies from about 1 to about 3.

Preferred amides are $C_8$–$C_{20}$ ammonia amides, monoethanolamides, diethanolamides, and isopropanolamides.

Cationic Surfactants—Cationic detersive surfactants can also be included in detergent compositions of the present invention. Cationic surfactants include the ammonium surfactants such as alkyldimethylammonium halogenides, and those surfactants having the formula:

$$[R^2(OR^3)_y][R^4(OR^3)_y]_2R^5N^+X^-$$

wherein $R^2$ is an alkyl or alkyl benzyl group having from about 8 to about 18 carbon atoms in the alkyl chain, each $R^3$ is selected from the group consisting of —CH$_2$CH$_2$—, —CH$_2$CH(CH$_3$)—, —CH$_2$CH(CH$_2$OH)—, —CH$_2$CH$_2$CH$_2$—, and mixtures thereof; each R$^4$ is selected from the group consisting of C$_1$–C$_4$ alkyl, C$_1$–C$_4$ hydroxyalkyl, benzyl, ring structures formed by joining the two R$^4$ groups, —CH$_2$CHOHCHOHCOR$^6$CHOH—CH$_2$OH wherein R$^6$ is any hexose or hexose polymer having a molecular weight less than about 1000, and hydrogen when y is not O; R$^5$ is the same as R$^4$ or is an alkyl chain wherein the total number of carbon atoms of R$^2$ plus R$^5$ is not more than about 18; each y is from 0 to about 10 and the sum of the y values is from 0 to about 15; and X is any compatible anion.

Other cationic surfactants useful herein are also described in U.S. Pat. No. 4,228,044, Cambre, issued Oct. 14, 1980, incorporated herein by reference.

Other Surfactants—Ampholytic surfactants can be incorporated into the detergent compositions hereof. These surfactants can be broadly described as aliphatic derivatives of secondary or tertiary amines, or aliphatic derivatives of heterocyclic secondary and tertiary amines in which the aliphatic radical can be straight chain or branched. One of the aliphatic substituents contains at least about 8 carbon atoms, typically from about 8 to about 18 carbon atoms, and at least one contains an anionic water-solubilizing group, e.g., carboxy, sulfonate, sulfate. See U.S. Pat. No. 3,929,678 to Laughlin et al., issued Dec. 30, 1975 at column 19, lines 18–35 for examples of ampholytic surfactants.

Zwitterionic surfactants can also be incorporated into the detergent compositions hereof. These surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 to Laughlin et al., issued Dec. 30, 1975 at column 19, line 38 through column 22, line 48 for examples of zwitterionic surfactants. Ampholytic and zwitterionic surfactants are generally used in combination with one or more anionic and/or nonionic surfactants.

Polyhydroxy Fatty Acid Amide Surfactant—The liquid detergent compositions hereof may also contain an enzyme-enhancing amount of polyhydroxy fatty acid amide surfactant. By "enzyme-enhancing" is meant that the formulator of the composition can select an amount of polyhydroxy fatty acid amide to be incorporated into the compositions that will improve enzyme cleaning performance of the detergent composition. In general, for conventional levels of enzyme, the incorporation of about 1%, by weight, polyhydroxy fatty acid amide will enhance enzyme performance.

The detergent compositions herein will typically comprise about 1% weight basis, polyhydroxy fatty acid amide surfactant, preferably from about 3% to about 30%, of the polyhydroxy fatty acid amide. The polyhydroxy fatty acid amide surfactant component comprises compounds of the structural formula:

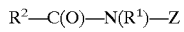

$$R^2—C(O)—N(R^1)—Z$$

wherein: R$^1$ is H, C$_1$–C$_4$ hydrocarbyl, 2-hydroxy ethyl, 2-hydroxy propyl, or a mixture thereof, preferably C$_1$–C$_4$ alkyl, more preferably C$_1$ or C$_2$ alkyl, most preferably C$_1$ alkyl (i.e., methyl); and R$^2$ is a C$_5$–C$_{31}$ hydrocarbyl, preferably straight chain C$_7$–C$_{19}$ alkyl or alkenyl, more preferably straight chain C$_9$–C$_{17}$ alkyl or alkenyl, most preferably straight chain C$_{11}$–C$_{15}$ alkyl or alkenyl, or mixtures thereof; and Z is a polyhydroxyhydrocarbyl having a linear hydrocarbyl chain with at least 3 hydroxyls directly connected to the chain, or an alkoxylated derivative (preferably ethoxylated or propoxylated) thereof. Z preferably will be derived from a reducing sugar in a reductive amination reaction; more preferably Z will be a glycityl. Suitable reducing sugars include glucose, fructose, maltose, lactose, galactose, mannose, and xylose. As raw materials, high dextrose corn syrup, high fructose corn syrup, and high maltose corn syrup can be utilized as well as the individual sugars listed above. These corn syrups may yield a mix of sugar components for Z. It should be understood that it is by no means intended to exclude other suitable raw materials. Z preferably will be selected from the group consisting of —CH$_2$—(CHOH)$_n$—CH$_2$OH, —CH(CH$_2$OH)—(CHOH)$_{n-1}$—CH$_2$OH, —CH$_2$—(CHOH)$_2$(CHOR')(CHOH)—CH$_2$OH, and alkoxylated derivatives thereof, where n is an integer from 3 to 5, inclusive, and R' is H or a cyclic or aliphatic monosaccharide. Most preferred are glycityls wherein n is 4, particularly —CH$_2$—(CHOH)$_4$—CH$_2$OH.

R' can be, for example, N-methyl, N-ethyl, N-propyl, N-isopropyl, N-butyl, N-2-hydroxy ethyl, or N-2-hydroxy propyl.

R$^2$—CO—N< can be, for example, cocamide, stearamide, oleamide, lauramide, myristamide, capricamide, palmitamide, tallowamide, etc.

Z can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

Methods for making polyhydroxy fatty acid amides are known in the art. In general, they can be made by reacting an alkyl amine with a reducing sugar in a reductive amination reaction to form a corresponding N-alkyl polyhydroxyamine, and then reacting the N-alkyl polyhydroxyamine with a fatty aliphatic ester or triglyceride in a condensation/amidation step to form the N-alkyl, N-polyhydroxy fatty acid amide product. Processes for making compositions containing polyhydroxy fatty acid amides are disclosed, for example, in G.B. Patent Specification 809,060, published Feb. 18, 1959, by Thomas Hedley & Co., Ltd., U.S. Pat. No. 2,965,576, issued Dec. 20, 1960 to E. R. Wilson, and U.S. Pat. No. 2,703,798, Anthony M. Schwartz, issued Mar. 8, 1955, and U.S. Pat. No. 1,985,424, issued Dec. 25, 1934 to Piggott, each of which is incorporated herein by reference.

Second Enzyme—Preferred compositions herein further comprise a performance-enhancing amount of a detergent-compatible second enzyme. By "detergent-compatible" is meant compatibility with the other ingredients of a liquid detergent composition, such as detersive surfactant and detergency builder. These second enzymes are preferably selected from the group consisting of lipase, amylase, cellulase, and mixtures thereof. The term "second enzyme" excludes the proteolytic enzymes discussed above, so each composition which has a second enzyme contains at least two kinds of enzyme, including at least one proteolytic enzyme. The amount of second enzyme used in the composition varies according to the type of enzyme. In general, from about 0.0001 to 0.3, more preferably 0.001 to 0.1, weight % of these second enzymes are preferably used. Mixtures of the same class of enzymes (e.g. lipase) or two or more classes (e.g. cellulase and lipase) may be used. Purified or non-purified forms of the enzyme may be used.

Any lipolytic enzyme suitable for use in a liquid detergent composition can be used in these compositions. Suitable lipase enzymes for use herein include those of bacterial and fungal origin.

Suitable bacterial lipases include those produced by microorganisms of the Pseudomonas groups, such as *Pseudomonas stutzeri* ATCC 19.154, as disclosed in British Patent 1,372,034, incorporated herein by reference. Suitable lipases include those which show a positive immunological cross-reaction with the antibody of the lipase produced by the microorganism *Pseudomonas fluorescens* IAM 1057. This lipase and a method for its purification have been described in Japanese Patent Application 53-20487, laid open on Feb. 24, 1978. This lipase is available from Amano Pharmaceutical Co. Ltd., Nagoya, Japan, under the trade name Lipase P "Amano," hereinafter referred to as "Amano-P." Such lipases should show a positive immunological cross-reaction with the Amano-P antibody, using the standard and well-known immunodiffusion procedure according to Ouchterlony (Acta. Med. Scan., 133, pages 76–79 (1950)). These lipases, and a method for their immunological cross-reaction with Amano-P, are also described in U.S. Pat. No. 4,707,291, Thom et al., issued Nov. 17, 1987, incorporated herein by reference. Typical examples thereof are the Amano-P lipase, the lipase ex *Pseudomonas fragi* FERM P 1339 (available under the trade name Amano-B), lipase ex *Pseudomonas nitroreducens* var. *lipolyticum* FERM P 1338 (available under the trade name Amano-CES), lipases ex *Chromobacter* viscosum, e.g. *Chromobacter viscosum* var. *lipolyticum* NRRLB 3673, commercially available from Toyo Jozo Co., Tagata, Japan; and further Chromobacter viscosum lipases from U.S. Biochemical Corp., U.S.A. and Disoynth Co., The Netherlands, and lipases ex *Pseudomonas gladioli*.

Suitable fungal lipases include those producible by *Humicola lanuginosa* and *Thermomyces lanuginosus*. Most preferred is lipase obtained by cloning the gene from *Humicola lanuginosa* and expressing the gene in *Aspergillus oryzae* as described in European Patent Application 0 258 068 (Novo Industri A/S), commercially available from Novo Nordisk A/S under the trade name Lipolase®.

From about 10 to 18,000, preferably about 60 to 6,000, lipase units per gram (LU/g) of lipase can be used in these compositions. A lipase unit is that amount of lipase which produces 1 mmol of titratable fatty acid per minute in a pH stat, where pH is 9.0, temperature is 30° C., substrate is an emulsion of 3.3 wt % of olive oil and 3.3% gum arabic, in the presence of 13 mmol/l $Ca^{++}$ and 20 mmol/l NaCl in 5 mmol/l Tris-buffer.

Any cellulase suitable for use in a liquid detergent composition can be used in these compositions. Suitable cellulase enzymes for use herein include those from bacterial and fungal origins. Preferably, they will have a pH optimum of between 5 and 9.5. From about 0.0001 to 0.1 weight % cellulase can be used.

Suitable cellulases are disclosed in U.S. Pat. No. 4,435,307, Barbesgaard et al., issued Mar. 6, 1984, incorporated herein by reference, which discloses fungal cellulase produced from *Humicola insolens*. Suitable cellulases are also disclosed in GB-A-2.075.028, GB-A-2.095.275 and DE-OS-2.247.832.

Examples of such cellulases are cellulases produced by a strain of *Humicola insolens* (*Humicola grisea* var. *thermoidea*), particularly the Humicola strain DSM 1800, and cellulases produced by a fungus of Bacillus N or a cellulase 212-producing fungus belonging to the genus Aeromonas, and cellulase extracted from the hepatopancreas of a marine mollusc (Dolabella Auricula Solander).

Any amylase suitable for use in a liquid detergent composition can be used in these compositions. Amylases include, for example, amylases obtained from a special strain of *B. licheniformis*, described in more detail in British Pat. No. Specification No. 1,296,839 (Novo). Amylolytic proteins include, for example, Rapidase$^R$, International Bio-Synthetics, Inc. and Ternamyl$^R$ Novo Industries.

From about 0.0001% to 0.55, preferably 0.0005 to 0.1, wt. % amylase can be used.

Calcium—The compositions herein may optionally comprise a calcium ion source. Any water-soluble calcium salt can be used as a source of calcium ions, including calcium acetate, calcium formate, calcium xylene sulfonate, and calcium propionate. Divalent ions, such as zinc and magnesium ions, can replace the calcium ion completely or in part. Thus in the liquid detergent compositions herein, the source of calcium ions can be partially substituted with a source of another divalent ion.

The calcium useful herein is enzyme-accessible. Therefore, the preferred compositions are substantially free of sequestrants, for example, polyacids capable of forming calcium complexes which are soluble in the composition. However, minor amounts of sequestrants such as polyacids or mixtures of polyacids can be used. The enzyme-accessible calcium is defined as the amount of calcium-ions effectively available to the enzyme component. From a practical standpoint the enzyme-accessible calcium is therefore the soluble calcium in the composition in the absence of any storage sequestrants, e.g., having an equilibrium constant of complexation with calcium equal to or greater than 1.5 at 20° C.

Boric Acid—The compositions herein also optionally contain from about 0.25% to about 10%, preferably from about 0.5% to about 5%, more preferably from about 0.75% to about 3%, by weight of boric acid or a compound capable of forming boric acid in the composition (calculated on the basis of the boric acid). Boric acid is preferred, although other compounds such as boric oxide, borax and other alkali metal borates (e.g., sodium ortho-, meta-, pyroborate, an sodium pentaborate) are suitable. Substituted boric acids (e.g., phenylboronic acid, butane boronic acid, and p-bromo phenylboronic acid) can also be used in place of boric acid.

The compositions of the present invention can also contain polyols, especially diols, containing only carbon, hydrogen and oxygen atoms. They preferably contain from about 2 to about 6 hydroxy groups. Examples include propylene glycol (especially 1,2 propanediol, which is preferred), ethylene glycol, glycerol, sorbitol, mannitol, glucose, and mixtures thereof. The polyol generally represents from about 1% to about 15%, preferably from about 1.5% to about 10%, more preferably from about 2% to about 7%, by weight of the composition.

Optional Ingredients—Detergent builders can optionally be included in the compositions herein, especially for laundry compositions. Inorganic as well as organic builders can be used. When present, the compositions will typically comprise at least about 1% builder and can be either an inorganic or organic builder. Liquid laundry formulations preferably comprise from about 3% to 30%, more preferably about 5 to 20%, by weight, of detergent builder.

Inorganic detergent builders include, but are not limited to, the alkali metal, ammonium and alkanolammonium salts of polyphosphates (exemplified by the tripolyphosphates, pyrophosphates, and glassy polymeric meta-phosphates), phosphonates, phytic acid, silicates, carbonates (including bicarbonates and sesquicarbonates), sulphates, and aluminosilicates. Borate builders, as well as builders containing borate-forming materials that can produce borate under detergent storage or wash conditions (hereinafter, collectively "borate builders"), can also be used. Preferably, non-borate builders are used in the compositions of the invention intended for use at wash conditions less than about 50° C., especially less than about 40° C.

Examples of silicate builders are the alkali metal silicates, particularly those having a $SiO_2:Na_2O$ ratio in the range 1.6:1 to 3.2:1 and layered silicates, such as the layered sodium silicates described in U.S. Pat. No. 4,664,839, issued May 12, 1987 to H. P. Rieck, incorporated herein by reference. However, other silicates may also be useful such as for example magnesium silicate, which can serve as a crispening agent in granular formulations, as a stabilizing agent for oxygen bleaches, and as a component of suds control systems.

Examples of carbonate builders are the alkaline earth and alkali metal carbonates, including sodium carbonate and sesquicarbonate and mixtures thereof with ultra-fine calcium carbonate as disclosed in German Pat. No. Application No. 2,321,001 published on Nov. 15, 1973, the disclosure of which is incorporated herein by reference.

Aluminosilicate builders are useful in the present invention. Aluminosilicate builders are of great importance in most currently marketed heavy duty granular detergent compositions, and can also be a significant builder ingredient in liquid detergent formulations. Aluminosilicate builders include those having the empirical formula:

$$M_z(zAlO_2 \cdot ySiO_2)$$

wherein M is sodium, potassium, ammonium or substituted ammonium, z is from about 0.5 to about 2; and y is 1; this material having a magnesium ion exchange capacity of at least about 50 milligram equivalents of $CaCO_3$ hardness per gram of anhydrous aluminosilicate. Preferred aluminosilicates are zeolite builders which have the formula:

$$Na_z[(AlO_2)_z(SiO_2)_y] \cdot xH_2O$$

wherein z and y are integers of at least 6, the molar ratio of z to y is in the range from 1.0 to about 0.5, and x is an integer from about 15 to about 264.

Useful aluminosilicate ion exchange materials are commercially available. These aluminosilicates can be crystalline or amorphous in structure and can be naturally-occurring aluminosilicates or synthetically derived. A method for producing aluminosilicate ion exchange materials is disclosed in U.S. Pat. No. 3,985,669, Krummel, et al., issued Oct. 12, 1976, incorporated herein by reference. Preferred synthetic crystalline aluminosilicate ion exchange materials useful herein are available under the designations Zeolite A, Zeolite P (B), and Zeolite X. In an especially preferred embodiment, the crystalline aluminosilicate ion exchange material has the formula:

$$Na_{12}[(AlO_2)_{12}(SiO_2)_{12}] \cdot xH_2O$$

wherein x is from about 20 to about 30, especially about 27. This material is known as Zeolite A. Preferably, the aluminosilicate has a particle size of about 0.1–10 microns in diameter.

Specific examples of polyphosphates are the alkali metal tripolyphosphates, sodium, potassium and ammonium pyrophosphate, sodium and potassium and ammonium pyrophosphate, sodium and potassium orthophosphate, sodium polymeta phosphate in which the degree of polymerization ranges from about 6 to about 21, and salts of phytic acid.

Examples of phosphonate builder salts are the water-soluble salts of ethane 1-hydroxy-1,1-diphosphonate particularly the sodium and potassium salts, the water-soluble salts of methylene diphosphonic acid e.g. the trisodium and tripotassium salts and the water-soluble salts of substituted methylene diphosphonic acids, such as the trisodium and tripotassium ethylidene, isopyropylidene benzylmethylidene and halo methylidene phosphonates. Phosphonate builder salts of the aforementioned types are disclosed in U.S. Pat. Nos. 3,159,581 and 3,213,030 issued Dec. 1, 1964 and Oct. 19, 1965, to Diehl; U.S. Pat. No. 3,422,021 issued Jan. 14, 1969, to Roy; and U.S. Pat. Nos. 3,400,148 and 3,422,137 issued Sep. 3, 1968, and Jan. 14, 1969 to Quimby, said disclosures being incorporated herein by reference.

Organic detergent builders preferred for the purposes of the present invention include a wide variety of polycarboxylate compounds. As used herein, "polycarboxylate" refers to compounds having a plurality of carboxylate groups, preferably at least 3 carboxylates.

Polycarboxylate builder can generally be added to the composition in acid form, but can also be added in the form of a neutralized salt. When utilized in salt form, alkali metals, such as sodium, potassium, and lithium, or alkanolammonium salts are preferred.

Included among the polycarboxylate builders are a variety of categories of useful materials. One important category of polycarboxylate builders encompasses the ether polycarboxylates. A number of ether polycarboxylates have been disclosed for use as detergent builders. Examples of useful ether polycarboxylates include oxydisuccinate, as disclosed in Berg, U.S. Pat. No. 3,128,287, issued Apr. 7, 1964, and Lamberti et al., U.S. Pat. No. 3,635,830, issued Jan. 18, 1972, both of which are incorporated herein by reference.

A specific type of ether polycarboxylates useful as builders in the present invention also include those having the general formula:

$$CH(A)(COOX)-CH(COOX)-O-CH(COOX)-CH(COOX)(B)$$

wherein A is H or OH; B is H or $-O-CH(COOX)-CH_2(COOX)$; and X is H or a salt-forming cation. For example, if in the above general formula A and B are both H, then the compound is oxydisuccinic acid and its water-soluble salts. If A is OH and B is H, then the compound is tartrate monosuccinic acid (TMS) and its water-soluble salts. If A is H and B is $-O-CH(COOX)-CH_2(COOX)$, then the compound is tartrate disuccinic acid (TDS) and its water-soluble salts. Mixtures of these builders are especially preferred for use herein. Particularly preferred are mixtures of TMS and TDS in a weight ratio of TMS to TDS of from about 97:3 to about 20:80. These builders are disclosed in U.S. Pat. No. 4,663,071, issued to Bush et al., on May 5, 1987.

Suitable ether polycarboxylates also include cyclic compounds, particularly alicyclic compounds, such as those described in U.S. Pat. Nos. 3,923,679; 3,835,163; 4,158,635; 4,120,874 and 4,102,903, all of which are incorporated herein by reference.

Other useful detergency builders include the ether hydroxypolycarboxylates represented by the structure:

$$HO-[C(R)(COOM)-C(R)(COOM)-O]_n-H$$

wherein M is hydrogen or a cation wherein the resultant salt is water-soluble, preferably an alkali metal, ammonium or substituted ammonium cation, n is from about 2 to about 15 (preferably n is from about 2 to about 10, more preferably n averages from about 2 to about 4) and each R is the same or different and selected from hydrogen, $C_{1-4}$ alkyl or $C_{1-4}$ substituted alkyl (preferably R is hydrogen).

Still other ether polycarboxylates include copolymers of maleic anhydride with ethylene or vinyl methyl ether, 1,3, 5-trihydroxy benzene-2,4,6-trisulphonic acid, and carboxymethyloxysuccinic acid.

Organic polycarboxylate builders also include the various alkali metal, ammonium and substituted ammonium salts of polyacetic acids. Examples include the sodium, potassium, lithium, ammonium and substituted ammonium salts of ethylenediamine tetraacetic acid, and nitrilotriacetic acid.

Also included are polycarboxylates such as mellitic acid, succinic acid, oxydisuccinic acid, polymaleic acid, benzene 1,3,5-tricarboxylic acid, and carboxymethyloxysuccinic acid, and soluble salts thereof.

Citrate builders, e.g., citric acid and soluble salts thereof (particularly sodium salt), are polycarboxylate builders of particular importance for heavy duty liquid detergent formulations, but can also be used in granular compositions.

Other carboxylate builders include the carboxylated carbohydrates disclosed in U.S. Pat. No. 3,723,322, Diehl, issued Mar. 28, 1973, incorporated herein by reference.

Also suitable in the detergent compositions of the present invention are the 3,3-dicarboxy-4-oxa-1,6-hexanedioates and the related compounds disclosed in U.S. Pat. No. 4,566,984, Bush, issued Jan. 28, 1986, incorporated herein by reference. Useful succinic acid builders include the $C_5$–$C_{20}$ alkyl succinic acids and salts thereof. A particularly preferred compound of this type is dodecenylsuccinic acid. Alkyl succinic acids typically are of the general formula R—CH(COOH)CH$_2$(COOH) i.e., derivatives of succinic acid, wherein R is hydrocarbon, e.g., $C_{10}$–$C_{20}$ alkyl or alkenyl, preferably $C_{12}$–$C_{16}$ or wherein R may be substituted with hydroxyl, sulfo, sulfoxy or sulfone substituents, all as described in the above-mentioned patents.

The succinate builders are preferably used in the form of their water-soluble salts, including the sodium, potassium, ammonium and alkanolammonium salts.

Specific examples of succinate builders include: laurylsuccinate, myristylsuccinate, palmitylsuccinate, 2-dodecenylsuccinate (preferred), 2-pentadecenylsuccinate, and the like. Laurylsuccinates are the preferred builders of this group, and are described in European Pat. No. Application 86200690.5/0,200,263, published Nov. 5, 1986.

Examples of useful builders, also include sodium and potassium carboxymethyloxymalonate, carboxymethyloxysuccinate, cis-cyclo-hexane-hexacarboxylate, cis-cyclopentane-tetracarboxylate, water-soluble polyacrylates (these polyacrylates having molecular weights to above about 2,000 can also be effectively utilized as dispersants), and the copolymers of maleic anhydride with vinyl methyl ether or ethylene.

Other suitable polycarboxylates are the polyacetal carboxylates disclosed in U.S. Pat. No. 4,144,226, Crutchfield et al., issued Mar. 13, 1979, incorporated herein by reference. These polyacetal carboxylates can be prepared by bringing together, under polymerization conditions, an ester of glyoxylic acid and a polymerization initiator. The resulting polyacetal carboxylate ester is then attached to chemically stable end groups to stabilize the polyacetal carboxylate against rapid depolymerization in alkaline solution, converted to the corresponding salt, and added to a surfactant.

Polycarboxylate builders are also disclosed in U.S. Pat. No. 3,308,067, Diehl, issued Mar. 7, 1967, incorporated herein by reference. Such materials include the water-soluble salts of homo- and copolymers of aliphatic carboxylic acids such as maleic acid, itaconic acid and methylenemalonic acid.

Other organic builders known in the art can also be used. For example, monocarboxylic acids, and soluble salts thereof, having long chain hydrocarbyls can be utilized. These would include materials generally referred to as "soaps." Chain lengths of $C_{10}$–$C_{20}$ are typically utilized. The hydrocarbyls can be saturated or unsaturated.

Other optional ingredients include soil release agents, chelating agents, clay soil removal/anti redeposition agents, polymeric dispersing agents, bleaches, brighteners, suds suppresors, solvents and aesthetic agents.

The detergent composition herein can be formulated as a variety of compositions, for instance as laundry detergents as well as hard surface cleaners or dishwashing compositions.

The compositions according to the present invention are further illustrated by the following examples.

EXAMPLE I

The following compositions are made by combining the listed ingredients in the listed proportions.

| Compositions | A | B | C | D | E | F |
|---|---|---|---|---|---|---|
| Linear alkyl benzene sulfonic acid | 8.5 | 15 | 6.5 | 10 | 12.5 | 4 |
| Sodium $C_{12-15}$ alkyl sulfate | 1 | 2 | 1 | 2 | — | — |
| $C_{12-15}$ alkyl 2.5 times ethoxylated sulfate | 10 | 5 | 10.5 | — | 11 | 9 |
| $C_{12}$ glucose amide | — | — | 9 | — | — | 5 |
| $C_{12-15}$ alcohol 7 times ethoxylated | 3 | 10 | 4 | 7 | 2.5 | — |
| Fatty acid | 2 | 5 | 5 | 4 | 2 | 2 |
| Citric acid | 6 | 7 | 4 | 6 | 4 | 5 |
| $C_{12-14}$ alkenyl substituted, succinic acid | — | 6 | — | 5 | — | 6 |
| Sodium hydroxide | 2 | 6 | 2 | 4 | 1 | 1.5 |
| Ethanol | 2 | 1.5 | 2 | 4 | 2 | 1.5 |
| Monoethanolamine | 6 | 5 | 4 | — | — | — |
| 1,2-Propanediol | 12 | 10 | 5 | 5 | 4 | 6 |
| Amylase (143 KNU/g) | — | — | 0.1 | — | — | 0.2 |
| Lipolase ® (100 KLU/g commercial solution) | 0.5 | 0.2 | 0.5 | 0.5 | 0.4 | — |
| Protease B (34 g/L commerical solution) | 0.9 | — | 0.5 | — | 1.2 | — |
| Savinase ® (commercial solution) | — | 0.3 | — | 0.4 | 0.2 | 0.3 |

EXAMPLE I-continued

The following compositions are made by combining the listed ingredients in the listed proportions.

| Compositions | A | B | C | D | E | F |
|---|---|---|---|---|---|---|
| Carezyme ® | 0.5 | 1 | 0.8 | — | 0.2 | 0.8 |
| Peptide aldehyde[1] | 0.009 | 0.005 | 0.001 | 0.0005 | 0.0003 | 0.01 |
| Calcium Ions | 0.01 | 0.5 | 0.1 | 0.05 | 0.9 | 0.25 |
| Water and minors | | | Balance to 100% | | | |

1) N-(methylsulfonyl)-Phe—Gly—Ala—LeuH which is prepared according to Synthesis Example 2.

EXAMPLE II

The following formula is prepared.

| Component | Wt (%) |
|---|---|
| Alkyl, 1.4 ethoxylated, sulfate | 30 |
| Amine oxide | 6 |
| Polyhydroxy fatty acid amide | 4 |
| Nonionic surfactant (C11E9) | 5 |
| Mg ion from MgCl$_2$ | 1 |
| Ca ion from CaCl$_2$ | 0.2 |
| Peptide aldehyde* | 0.0025 |
| Sodium xylene sulfonate | 4 |
| Solvent | 6 |
| Water | to 100% |
| pH | to 8 |

*Peptide Aldehyde of Synthesis Example 2.

EXAMPLE III

The following compositions are made by combining the listed ingredients in the listed proportions.

| Ingredients | A (wt %) | B (wt %) | C (wt %) | D (wt %) |
|---|---|---|---|---|
| LAS | 0 | 0 | 0 | 12 |
| AExS[1] | 22.1 | 24.7 | 33.5 | 3 |
| Polyhydroxy fatty acid amide | 4.6 | 1.2 | 4.2 | 0 |
| Amine Oxide | 4.6 | 1.2 | 4.8 | 0 |
| Betaine | 0 | 1.2 | 0 | 0 |
| Nonionic Surfactant | 6.7 | 4.1 | 0 | 0 |
| Mg(OH)$_2$ | 0.5 | 0.5 | 0.7 | 0 |
| Ca ion from CaCl$_2$ | 0.1 | 0.3 | 0.4 | 0.1 |
| Calcium xylene sulfonate | 4.5 | 0 | 4 | 0 |
| Polyethylene glycol | 3 | 0 | 0 | 0 |
| Polypropylene glycol 2000 | 1.5 | 0 | 0 | 0 |
| Balance, water | to 100% | to 100% | to 100% | to 100% |
| Protease A or Protease B | 0.001–0.01 | 0.001–0.01 | 0.005–0.01 | 0.0003–0.01 |
| Peptide Aldehyde[2] | 0.00025–0.0025 | 0.00025–0.0025 | 0.00025–0.0025 | 0.00125–0.0025 |

[1]x = the degree of ethoxylation. The average degree of ethoxylation for the compositions are: A = 2.2, B = 0.6, C = 1.4, D = 2.2.
[2]The peptide aldehyde of Synthesis Example 2 is used herein.

What is claimed is:

1. A liquid detergent composition comprising:

a) from about 1% to about 95% by weight of detersive surfactant;

b) from about 0.0001% to about 5% by weight of an active proteolytic enzyme; and c) from about 0.00001% to about 5% by weight of a peptide protease inhibitor having the formula:

Z—B—NH—CH(R)—C(O)—X wherein B is a peptide chain comprising from 2 to 5 amino acid moieties; X is hydrogen or CF$_3$; Z is an N-capping moiety selected from the group consisting of sulfonamides, phosphonamides, thioureas, sulfenamides, sulfonic acids, phosphinamides, thiocarbamates, amidophosphates, and sulfamoyl derivatives; and R is selected from the group consisting of straight or branched C$_1$–C$_6$ unsubstituted alkyl, phenyl, and C$_7$–C$_9$ alkylaryl moieties.

2. A liquid detergent composition according to claim 1 wherein the R is selected from the group consisting of methyl, iso-propyl, sec-butyl, iso-butyl, —C$_6$H$_5$, —CH$_2$—C$_6$H$_5$, and —CH$_2$CH$_2$–C$_6$H$_5$.

3. A liquid detergent composition according to claim 2 further comprising a source of calcium ions.

4. A liquid detergent composition according to claim 1 wherein the N-capping Z moiety is selected from the group consisting of (R"O)$_2$(O)P—, (SR")$_2$—, R"(O)$_2$S—, SO$_3$H, (R")$_2$(O)P—, R"O(O)$_2$S—, (R")$_2$N(O)C—, R"O(S)C—, R"—P(O)OH, and R"O(OH)(O)P—, wherein each R" is independently selected from the group consisting of straight or branched C$_1$–C$_6$ unsubstituted alkyl, phenyl, C$_7$–C$_9$ alkylaryl, and cycloalkyl moieties, wherein the cycloalkyl ring may span C$_4$–C$_8$ and may contain one or more heteroatoms selected from the group consisting of O, N, and S.

5. A liquid detergent composition according to claim 4 further comprising a source of calcium ion selected from calcium formate, calcium chloride, calcium acetate, calcium xylene sulfonate, calcium sulfate, and mixtures thereof.

6. A liquid detergent composition according to claim 5 wherein said proteolytic enzyme is a subtilisin-type protease.

7. A liquid detergent composition according to claim 6 wherein said proteolytic enzyme is selected from the group consisting of bacterial serine proteolytic enzymes obtained from *Bacillus subtilis*, bacterial serine proteolytic enzymes obtained from *Bacillus licheniformis*, modified bacterial serine proteolytic enzymes and mixtures thereof.

8. A liquid detergent composition according to claim 7 wherein said composition is a light duty detergent composition suitable for dishcare.

9. A liquid dishcare detergent composition according to claim 8 further comprising one or more of the following: suds boosters, chelants, polyacrylate polymers, dispersing agents, dyes, perfumes, processing aids, and mixtures thereof.

10. A liquid dishcare detergent composition according to claim 9 further comprising amylase enzyme.

11. A liquid dishcare detergent composition according to claim 10 further comprising from about from about 0.25% to about 10% by weight of boric acid or a compound capable of forming boric acid and a polyol.

12. A liquid detergent composition according to claim 7 wherein said composition is a heavy duty detergent composition suitable for laundrycare.

13. A liquid laundry detergent composition according to claim 12 further comprising an effective amount one or more of the following second enzymes: lipase, amylase, cellulase, and mixtures thereof.

14. A liquid laundry detergent composition according to claim 13 further comprising one or more of the following: suds boosters, builders, soil release polymers, polyacrylate polymers, dispersing agents, dye transfer inhibitors, dyes, perfumes, processing aids, brighteners, and mixtures thereof.

15. A liquid laundry detergent composition according to claim 13 wherein said second enzyme is lipase.

16. A liquid laundry detergent composition according to claim 15 wherein the lipase is obtained by cloning the gene from *Humicola Lanuginosa* and expressing the gene in *Aspergillus Oryzae*.

17. A composition according to claim 13 wherein said second enzyme is a cellulase derived from *Humicola Insolens* and wherein said composition comprises from 0.0001% to 0.1% by weight of the total composition of said cellulase.

18. A liquid laundry detergent composition according to claim 12 further comprising from about from about 0.25% to about 10% by weight of boric acid or a compound capable of forming boric acid and a polyol.

19. The peptide compounds $CH_3SO_2$Phe-Gly-Ala-Leu-H, $CH_3SO_2$Val-Ala-Leu-H, $C_6H_5CH_2O(OH)(O)$P-Val-Ala-Leu-H, $C_6H_5CH_2O(OH)(O)$P-Val-Ala-Leu-$CF_3$, $CH_3CH_2SO_2$-Phe-Gly-Ala-Leu-H, $C_6H_5CH_2SO_2$-Val-Ala-Leu-H, $C_6H_5CH_2O(OH)(O)$P-Leu-Ala-Leu-H, $C_6H_5CH_2O(OH)(O)$P-Phe-Ala-Leu-H, and $CH_3O(OH)(O)$P-Leu-Gly-Ala-Leu-H.

20. A liquid detergent composition comprising:
   a) from about 1% to about 95% by weight of detersive surfactant;
   b) from about 0.0001% to about 5% by weight of an active proteolytic enzyme; and
   c) from about 0.00001% to about 5% by weight of a peptide protease inhibitor having the formula:

Z—B—NH—CH(R)—C(O)—CF$_3$ wherein B is a peptide chain comprising from 2 to 5 amino acid moieties; Z is an N-capping moiety selected from the group consisting of sulfonamides, phosphonamides, thioureas, sulfenamides, sulfonic acids, phosphinamides, thiocarbamates, amidophosphates, and sulfamoyl derivatives; and R is selected from the group consisting of straight or branched $C_1$–$C_6$ unsubstituted alkyl, phenyl, and $C_7$–$C_9$ alkylaryl moieties.

21. A liquid detergent composition comprising:
   a) from about 1% to about 95% by weight of detersive surfactant;
   b) from about 0.0001% to about 5% by weight of an active proteolytic enzyme; and
   c) from about 0.00001% to about 5% by weight of a peptide protease inhibitor having the formula:

Z—B—NH—CH(R)—C(O)—X wherein B is a peptide chain comprising from 2 to 5 amino acid moieties; X is hydrogen or CF$_3$; Z is an N-capping moiety selected from the group consisting of phosphonamides, thioureas, sulfenamides, phosphinamides, thiocarbamates, and amidophosphates; and R is selected from the group consisting of straight or branched $C_1$–$C_6$ unsubstituted alkyl, phenyl, and $C_7$–$C_9$ alkylaryl moieties.

* * * * *